(12) United States Patent
Zehner et al.

(10) Patent No.: US 6,624,315 B2
(45) Date of Patent: Sep. 23, 2003

(54) METHOD OF GAS PHASE CATALYTIC OXIDATION TO GIVE MALEIC ACID ANHYDRIDE

(75) Inventors: Peter Zehner, Ludwigshafen (DE); Otto Machhammer, Mannheim (DE); Claus Hechler, Ludwigshafen (DE); Alexander Weck, Freinsheim (DE); Gerhard Olbert, Dossenheim (DE); Uwe Stabel, Otterstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/936,347

(22) PCT Filed: Jan. 10, 2001

(86) PCT No.: PCT/EP01/00234

§ 371 (c)(1),
(2), (4) Date: Sep. 11, 2001

(87) PCT Pub. No.: WO01/51448

PCT Pub. Date: Jul. 19, 2001

(65) Prior Publication Data

US 2002/0161243 A1 Oct. 31, 2002

(30) Foreign Application Priority Data

Jan. 10, 2000 (DE) .......................................... 100 00 584

(51) Int. Cl.[7] ............................................ C07D 307/60

(52) U.S. Cl. ........................ 549/259; 549/256; 549/257; 549/258; 549/260

(58) Field of Search ................................ 549/256, 257, 549/258, 259, 260

(56) References Cited

U.S. PATENT DOCUMENTS

| | | | |
|---|---|---|---|
| 4,077,912 A | 3/1978 | Dolhyj et al. ............... | 252/461 |
| 4,544,544 A | 10/1985 | Dang Vu et al. ............ | 423/659 |
| 6,172,244 B1 | 1/2001 | Heisel ........................ | 549/534 |

FOREIGN PATENT DOCUMENTS

| | | |
|---|---|---|
| DE | 2 016 614 | 10/1971 |
| DE | 2 351 151 | 10/1972 |
| DE | 197 19 375 | 11/1998 |
| DE | 197 54 185 | 2/1999 |
| DE | 198 57 842 | 6/2000 |
| DE | 100 31 347 | 1/2001 |
| WO | WO 99/29416 | 6/1999 |
| WO | WO 00/35574 | 6/2000 |
| WO | WO 01/32301 | 5/2001 |

*Primary Examiner*—Bernard Dentz
(74) *Attorney, Agent, or Firm*—Keil & Weinkauf

(57) ABSTRACT

A process for the preparation of maleic anhydride by heterogeneously catalyzed gas-phase oxidation in a reactor with feed for the reaction mixture at one end of the reactor and discharge of the product mixture at the opposite end of the reactor, and with devices for dissipating the heat of reaction which are arranged in the reactor interior and through which a heat-exchange medium flows and which are designed as heat-exchanger plates.

10 Claims, 6 Drawing Sheets

8

METHOD OF GAS PHASE CATALYTIC OXIDATION TO GIVE MALEIC ACID ANHYDRIDE

The present invention relates to a process for the preparation of maleic anhydride by heterogeneously catalyzed gas-phase oxidation.

Maleic anhydride has considerable industrial importance. For example, it can be used for both condensation polymerization and addition polymerization, with polyester resins and alkyd resins being the most important industrial secondary products. In addition, maleic anhydride is the starting material for commercially important chemicals, such as succinic anhydride, gamma-butyrolactone, 1,4-butanediol and tetrahydrofuran.

In known commercial-scale processes for gas-phase oxidation to give maleic anhydride, a reaction mixture comprising n-butane, oxygen and further components, such as nitrogen and steam, is converted at from 320 to 480° C. in a catalyst bed consisting of individual particles into a reaction mixture which, besides the principal component maleic anhydride, furthermore comprises steam, carbon monoxide, carbon dioxide, unreacted butane, inert gases, for example nitrogen, and further organic trace components. The enthalpy of reaction liberated during the process heats the reaction mixture. Strong warming of the reaction mixture reduces the yield of the desired valuable product maleic anhydride due to nonselective superoxidation, with very strong warming entailing the risk of the reaction becoming a combustion reaction in the gas phase, with a considerable increase in temperature and pressure.

In order to be able to limit the increase in temperature, some of the enthalpy of reaction is therefore dissipated in the reactors employed via the reactor walls surrounding the catalyst. For this purpose, the reaction space is divided into a large number of parallel individual reaction spaces in the form of tubes having an internal diameter of from 20 to 45 mm. Reaction mixture flows from top to bottom through the vertical individual tubes filled with catalyst bed, with more than 60% of the enthalpy of reaction being released via the tube wall to a heat-exchange medium flowing around the tubes. The heat-exchange medium used is generally an inorganic salt melt, but it is also possible to use organic heat-exchange media, metal melts or gases, such as helium. In order to limit the warming of the heat-exchange medium in the reactor to less than 20° C., high circulation quantities and corresponding pump capacities are necessary. Re-cooling of the heat-exchange fluid is usually carried out by the generation of steam at tubes through or around which the heat-exchange medium flows.

For high selectivity of the reaction, it is necessary to limit the axial and radial temperature gradients in the reaction tube to less than 30° C. For the axial temperature gradient, the internal preheating zone in the reaction tube, in which the reaction mixture is heated to the reaction temperature, and which can also be positioned in a heat exchanger upstream of the actual reactor, remains out of consideration. The maximum permissible radial temperature gradient determines the maximum tube diameter, while the minimum gas velocity necessary for adequate convective heat transfer in the tube filled with catalyst bed, together with the specific reaction rate, determines the minimum tube length. In order to meet these requirements, the reactors for commercial-scale processes generating about 30,000 metric tons per annum of maleic anhydride contain from 12,000 to 40,000 reaction tubes connected in parallel. The minimum tube length and the minimum gas velocity in turn result in a loss of flow pressure over the reactor of greater than 0.4 bar. In order to avoid nonuniform flow into the reaction tubes and thus corresponding selectivity losses and the risk of changeover into a homogeneous combustion reaction in the gas phase due to local overheating, the pressure loss in each of the numerous reaction tubes is therefore usually equalized in a complex manner. The filling of the reaction with catalyst and the removal thereof are therefore very time-consuming and expensive.

Reactors of this type thus have firstly the disadvantage that a very large number of individual reaction tubes are necessary, resulting in a complex design and high costs. In addition, it is disadvantageous that an intermediate circuit containing a heat-exchange medium is necessary, which in turn means that high pump capacities are necessary and additional costs arise for re-cooling of the heat-exchange medium. In addition, a loss of exergy occurs. A further disadvantage is that the high pressure loss in the individual reaction tubes and the equalization necessary therefor result in very complex handling of the catalyst.

DE-C-197 54 185 describes, for example, a reactor having a cylindrical reactor tank, with heat-exchanger plates in the form of thermal plates being arranged alongside one another at a prespecified spacing from one another in the reactor tank in vertical orientation on the perforated base of the reactor. A cooling medium which is fed to the heat-exchanger plates via suitable devices in the region of the tank lid and is discharged from the heat-exchanger plates via suitable devices in the region of the tank base flows through the plates. A gaseous reaction medium is passed between the heat-exchanger plates in countercurrent to the cooling medium, with feeding in the region of the tank base and discharge in the region of the tank lid. The specification gives absolutely no indication that a reactor of this type can be employed for heterogeneously catalyzed gas-phase oxidation to give maleic anhydride.

DE-A-197 19 375 describes a process for the preparation of ethylene oxide by catalytic gas-phase oxidation of ethylene using oxygen in a reactor, where the catalyst is arranged in reaction zones between heat-exchanger plates, and the gaseous reaction mixture flows through the catalyst. In catalytic gas-phase oxidation to give ethylene oxide, a comparatively small amount of heat is developed per volume unit of the catalyst.

It is an object of the present invention to provide a process for the preparation of maleic anhydride which exhibits increased economic efficiency, in particular with respect to the consumption of heat-exchange medium, even at very high conversions and in plants of large capacity.

We have found that this object is achieved by carrying out the heterogeneously catalyzed gas-phase oxidation to give maleic anhydride in a reaction space between heat-exchanger plates and thus in a two-dimensional catalyst bed which extends beyond the reactor cross section. Surprisingly, an unforeseeable increase in selectivity of the formation of maleic anhydride has been found here.

The invention thus relates to a process for the preparation of maleic anhydride by heterogeneously catalyzed gas-phase oxidation in a reactor with feed for the reaction mixture at one end of the reactor and discharge of the product mixture at the opposite end of the reactor, and with devices for dissipating the heat of reaction which are arranged in the reactor interior and through which a heat-exchange medium flows, wherein the devices are heat-exchanger plates.

Preferred embodiments of the invention are defined in the following description, the figures and the dependent claims.

The starting compounds used can in principle be any starting materials known for the preparation of maleic anhydride, in particular n-butane, n-butene or mixtures thereof, and benzene or butadiene. The most preferred is the preparation from n-butane. The catalytic gas-phase oxidation using molecular oxygen or a gas containing the latter, for example air, is advantageously carried out, with air being particularly preferred. In addition, the reaction mixture may also comprise further components, for example nitrogen, steam or other inertizing diluent gases, for example carbon dioxide, carbon monoxide, isobutane and/or methane.

The gas-phase oxidation is preferably carried out at temperatures in the range from 320° to 480° C., in particular from 380° to 450° C., and, where appropriate, superatmospheric pressure, preferably at a pressure of from 1 to 6 bar absolute.

It is possible to employ any heterogeneous catalyst which is known in the prior art for the preparation of maleic anhydride. Preferred heterogeneous catalysts are oxidic multicomponent catalysts based on the oxides of vanadium and phosphorus (so-called V—P—O catalysts), for example $(VO)_2P_2O_7$. These catalysts may be mixed with promoters, for example zinc, zirconium, bismuth, antimony, tin, nickel, cobalt, iron, chromium, manganese and/or molybdenum. On use of benzene as starting compound, it is also possible to employ catalysts based on the oxides of vanadium and molybdenum. The shape of the catalyst is not subject to any particular restriction. Any solid geometrical shape which comprises individual particles and contains pores can be used. The catalyst particles can have, for example, a cylindrical, cubic, conical, prismatic, pyramidal or trilobal shape. The catalyst preferably consists of individual particles having a hydraulic diameter in the range from 3 to 8 mm. The catalyst can also be in the form of a supported catalyst, as described, for example, in DE-A 2 351 151, in which the catalytically active material is applied to an inert support. It is also possible to employ catalysts of different activity and/or different shape simultaneously, where, for better control of the properties of the catalyst, small amounts of a phosphorus compound, in particular an organophosphorus compound, may also be added to the reaction mixture. The properties of the catalyst can also be controlled by using catalyst particles of different size or additionally inert solid materials as diluent.

Suitable reaction mixtures comprise from 0.5 to 10% by volume of the above-mentioned starting compound, from 6 to 30% by volume of oxygen and the remainder of further components, for example nitrogen, steam and/or other inertizing diluent gases, in particular as defined above, in each case based on 100% by volume of reaction mixture.

The catalytic gas-phase oxidation of $C_4$ starting compounds does not give pure maleic anhydride, but instead a product mixture which, in addition to maleic anhydride, comprises, for example, acetic acid, acrylic acid, crotonic acid, carbon monoxide, carbon dioxide, unreacted starting compounds, etc., as secondary components. The product mixture usually comprises, in each case based on the product mixture as a whole, from 0.2 to 4% by volume of maleic anhydride, from 0.01 to 0.09% by volume of each of acetic acid and/or acrylic acid, and the remainder of nitrogen, carbon dioxide, carbon monoxide, steam and/or further inertizing diluent gases. In the oxidation of benzene, small amounts of benzoquinone, formaldehyde and formic acid arise as by-products.

The shape of the reactor is in principle not subject to any restrictions. Conventional cylindrical reactors, but also cuboid reactors can be employed. There are likewise no restrictions regarding the orientation of the reactors; the reactors can in principle be oriented in any position, with a vertical orientation generally being preferred for the special case of cylindrical reactors.

In accordance with the invention, reactors having devices for dissipating the heat of reaction, which are designed as heat-exchanger plates, are employed for the process for the gas-phase oxidation to give maleic anhydride. In a preferred embodiment of the invention, at least 60% of the enthalpy of reaction liberated in the reactor are dissipated via the heat-exchanger plates. Some of the enthalpy of reaction can also be dissipated with the reaction gas, or part of the heat-exchange surface area can be provided in the reactor in a conventional manner. In this case, part of the heat-exchange surface area may also be surrounded by gas space (intermediate condenser) or inert material (prewarming zone, secondary condenser).

Heat-exchanger plates are predominantly two-dimensional structures which have an internal space of small thickness relative to the surface area which is provided with feed and discharge lines. They are generally made from metal sheeting, frequently from steel sheeting. Depending on the application, in particular the properties of the reaction medium and of the heat-exchange medium, however, special, in particular corrosion-resistant materials can be used. The feed and discharge devices for the heat-exchange medium are generally arranged at opposite ends of the heat-exchanger plates. The heat-exchanger plates preferably consist of at least two metal sheets connected in a pressure-tight manner at the periphery and supported against one another in a 15 to 80 mm grid by punctiform bonding, preferably spot welding, and expanded by internal pressure, with the heat-exchange medium flowing through their internal space formed in this way. In a particularly preferred embodiment, the heat-exchanger plates have a width of from 0.5 to 3 m, a maximum length of 8 m and an overall thickness of from 5 to 100 mm. In a further preferred embodiment, the heat-exchanger plates are constructed from at least four individual sheets in such a way that two preferably gas-filled insulating pockets surrounding the central pocket through which heat-exchange medium flows are formed.

With respect to the arrangement of the heat-exchanger plates in the reactor, there are in principle no restrictions; the heat-exchanger plates may be arranged, for example, spirally, concentrically or radially in the reactor. They can also be suspended in the casing tube of the reactor. They are preferably layered to give plane-parallel packages, bent to give rings or ring segments and then arranged concentrically, or bent in a spiral manner, with an intermediate space of at least 4 mm and at most 60 mm preferably remaining between the plates. It is also possible to position plate packages at an inclination, where at least one package of sheets is arranged in such a way that the flow channels formed by the plates form an angle of from 0 to 20° with the central axis of the reactor. The surface of the heat-exchanger plates may also be provided with a spacer as far as the catalyst layer, which is preferably carried out by application of an expanded metal mesh or inert material. In addition, individual plate packages can be operated at different heat-exchange medium temperatures, with the temperature along the reactor axis varying. Temperature zoning of this type enables matching to different heat flow densities. In addition, the plate separation of the individual plate packages in the flow direction can increase in accordance with the decrease in performance density with increasing reaction progress, which supplements and/or replaces the abovementioned temperature zoning.

It is also advantageous to employ heat-exchanger plates which have a wedge shape, i.e. their interior space through which heat-exchange medium flows preferably decreases continuously in the direction of the reaction-mixture stream. Wedge-shaped heat-exchanger plates of this type can be produced, for example, by placing two sheets on one another and welding them at increasing separations. The plates are subsequently clamped into an easily tilted blow-up device and blown up to a prespecified separation. The matching to the temperature profile of the reaction can be optimized by means of heat-exchanger plates formed in a wedge shape. In a further advantageous embodiment, the heat-exchanger plates can be welded over all or some of their length. To this end, in each case two sheets are laid one on top of the other, welded by roll seam welding over longitudinal seams and blown up by means of a suitable blow-up device.

In accordance with a further embodiment, planar, rectangular sheets oriented parallel to one another are introduced into the reactor interior so that they essentially fill the latter completely, where the edges of two opposite sides of each sheet are beveled at right angles in the same direction and, in the respective subsequent sheets, the edges of the other two opposite sides are beveled at right angles in the same direction at the same separation so as to form in each case cuboid spaces, with the reaction mixture or heat-exchange medium flowing through the respective adjacent spaces in cross-current.

According to a further embodiment, heat-exchanger plates are arranged parallel to one another in the longitudinal direction of the reactor.

In a further variant, plate packages are offset in such a way that the orientation of the plate transverse axis differs by from 0 to 90° between at least two successive plate packages.

Regarding the heat-exchange medium which can be employed in the process according to the invention, there are in principle no restrictions. It is possible to employ both inorganic and organic liquid heat-exchange media which remain in the liquid physical state or partially or fully evaporate at the reaction temperature of the catalyst gas-phase oxidation. A salt melt, for example, is particularly suitable. In addition, it is also possible to employ gaseous heat-exchange media, preferably helium. It is particularly advantageous to employ a heat-exchange medium which evaporates fully or at least partially at the reaction temperature of the catalytic gas-phase oxidation. Water is particularly preferred for this purpose. By utilizing evaporative cooling, efficient heat dissipation is ensured here, a significant saving of the amount necessary being achieved for the dissipation of the same amount of heat compared with the use of a heat-exchange medium which does not change its physical state. In a preferred embodiment, high-boiling substances, preferably polyhydric alcohols, are added to the heat-exchange medium for the purposes of raising the boiling point, or these alcohols are used in pure form.

Evaporative cooling can take place both in cocurrent and in countercurrent. In the case of operation in cocurrent with inflow from below, it is additionally possible to regulate the level of the boiling liquid in such a way that low heat dissipation takes place toward the end of the reactor, and the now higher temperature level there results in an increase in the overall yield. In the case of evaporative cooling, a defined vapor pressure (values in the range from about 20 to 160 bar in the case of water) becomes established on the cooling-medium side in accordance with the temperature, making a correspondingly pressure-tight design of the cooling-medium side of the apparatus necessary.

In a further preferred embodiment of the invention, a mixture of heat-exchange medium vapor and liquid in the form of bubbles, drops and/or an aerosol flows through the heat-exchanger plates. Sufficient heat-exchange medium that the heat transfer takes place substantially via the gas phase and is thus intentionally impaired can be specifically sprayed in.

In accordance with the invention, the reaction mixture at one end of the reactor is fed to the reactor internal space between the heat-exchanger plates and discharged at the opposite end of the reactor. The reaction mixture thus flows through the reactor through the interspace between the heat-exchanger plates. Constant cross-mixing of the reaction mixture thus takes place, with the consequence of high homogeneity thereof.

The heat-exchange medium and reaction mixture can be passed through the reactor in cocurrent, countercurrent or cross current. The cocurrent variant is particularly preferred since this ensures better matching to the temperature profile of the reaction.

According to a further preferred embodiment, two or more reaction zones with separate heat-exchange medium circuits can be arranged in the direction of the reaction mixture flow.

The catalyst can be introduced into the interspace between the heat-exchanger plates, for example in the form of an unordered bed. The introduction and change of the catalyst bed is in this case simpler and more uniform compared with introduction into the reaction tubes in known processes. Larger coherent reaction spaces are formed, and the risk of blockage of the catalyst bed is lower. In the case of arrangement of the catalyst in a bed around the heat-exchanger plates, it is advantageous that, in the case of local dislocations, the reaction gas can redistribute itself again over the full catalyst cross section between two heat-exchanger plates after flowing past the restriction and the whole reaction cross section can contribute to the conversion. A further advantage of heat-exchange plates is the easier emptying of the catalyst in the case of catalyst change compared with the tube-bundle reactor.

However, it is also possible, in addition or as an alternative to the catalyst bed, to provide the heat-exchanger plates with a catalytic coating on their outsides over which the reaction mixture flows. In this case, the catalyst is applied directly to the plates in a layer thickness in the range from 0.1 to 1.5 mm. The plates to be coated are preferably pretreated by mechanical methods, for example sand blasting, ball blasting or chemical methods, for example etching or precoating. Owing to the essentially planar shape of the heat-exchanger plates, they are simpler to coat compared with reaction tubes.

The process according to the invention thus comprises the following features and advantages.

Simple design with replaceable heat-exchanger plates; on use of standardized sheets for the plates, further costs can be saved;

high pressure resistance enables selective cooling with generation of direct steam, with no intermediate circuits being necessary; consequently low specific heat-exchange medium throughput and thus lower pump capacity and reduced loss of exergy;

the catalyst is in the broadest sense in the form of a "homogeneous phase" in the reactor (continuous bed), which enables cross-equalization of pressure, temperature and composition; this results in less formation of "hot flow channels", and consequently in suppression of the highest temperatures in the reactor, the so-called hot spots, and furthermore in lower pressure loss in the reactor, making equalization of the individual reaction tubes employed in known processes unnecessary;

handling of the catalyst is significantly simplified; a preliminary zone or a guard bed is possible through simple filling of the reactor to above the uppermost plate package.

The invention is explained in greater detail below with reference to figures, which represent preferred embodiments of the invention.

In the figures, identical or corresponding features are provided with identical reference numerals.

FIG. 1 shows a longitudinal section through a particularly preferred embodiment of a reactor which is particularly suitable for carrying out the process, FIG. 1a shows a cross section through the reactor from FIG. 1, FIG. 1b shows a longitudinal section through a heat-exchanger plate in the reactor from FIG. 1, FIG. 1c shows a preferred arrangement of the weld points on the heat-exchanger plate from FIG. 1b, FIG. 2 shows a longitudinal section through a reactor which is particularly suitable for carrying out the process, with reaction mixture and heat-exchange medium flowing in cocurrent, FIG. 3 shows a longitudinal section through a further preferred embodiment of a reactor which is particularly suitable for carrying out the process, with the reaction mixture and heat-exchange medium flowing in countercurrent, FIG. 4 shows a longitudinal section through a cuboid reactor which is suitable for carrying out the process, FIG. 4a shows an enlarged section from the reactor shown in FIG. 4 in order to illustrate the construction of the reactor plates, FIG. 4b shows a cross section through the reactor shown in FIG. 4, and FIG. 5 shows a longitudinal section through a reactor being suitable for carrying out the process, said reactor having, by way of example, three reaction zones.

The reactor shown in longitudinal section in FIG. 1 has the shape of a cylinder with feed of the reaction mixture (1) in the upper region and discharge of the product mixture (2) in the lower reactor region. The reaction mixture (1) is passed over the catalyst bed (5). Heat-exchanger plates (8) having a wedge-shaped design are arranged in the reactor internal space in the longitudinal direction of the reactor. A heat-exchange medium introduced via a feed (3) and a distributor line (6) and discharged via a collecting line (7) and a discharge line (4) flows through the reactor plates. The cross section in FIG. 1a illustrates the essentially parallel arrangement of the heat-exchanger plates (8).

FIGS. 1b and 1c illustrate the wedge-shaped design of the heat-exchanger plates (8) and their construction by sheets spot-welded to one another.

FIG. 2 shows by way of example a longitudinal section through a reactor with the reaction mixture and heat-exchange medium flowing in cocurrent. FIG. 2 makes it clear that the liquid level of the heat-exchange medium in the heat-exchanger plates (8) only goes up to a certain height, i.e. the heat-exchange medium evaporates above this. Heat dissipation thus takes place by evaporative cooling.

FIG. 4 shows a longitudinal section through a cuboid reactor; the design of the heat-exchanger plate (8) is made clear in the section shown enlarged in FIG. 4a.

Figure 1A:
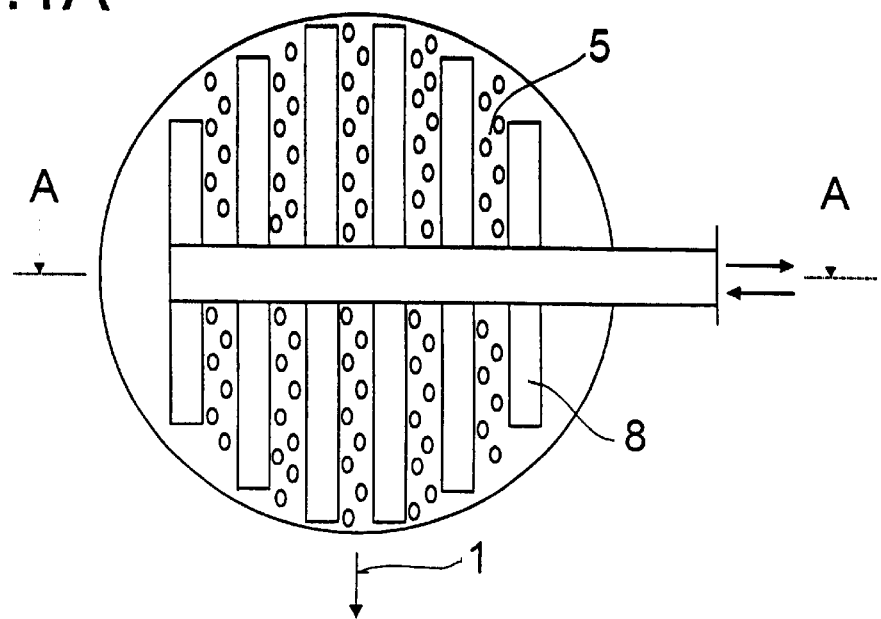
Figure 1:
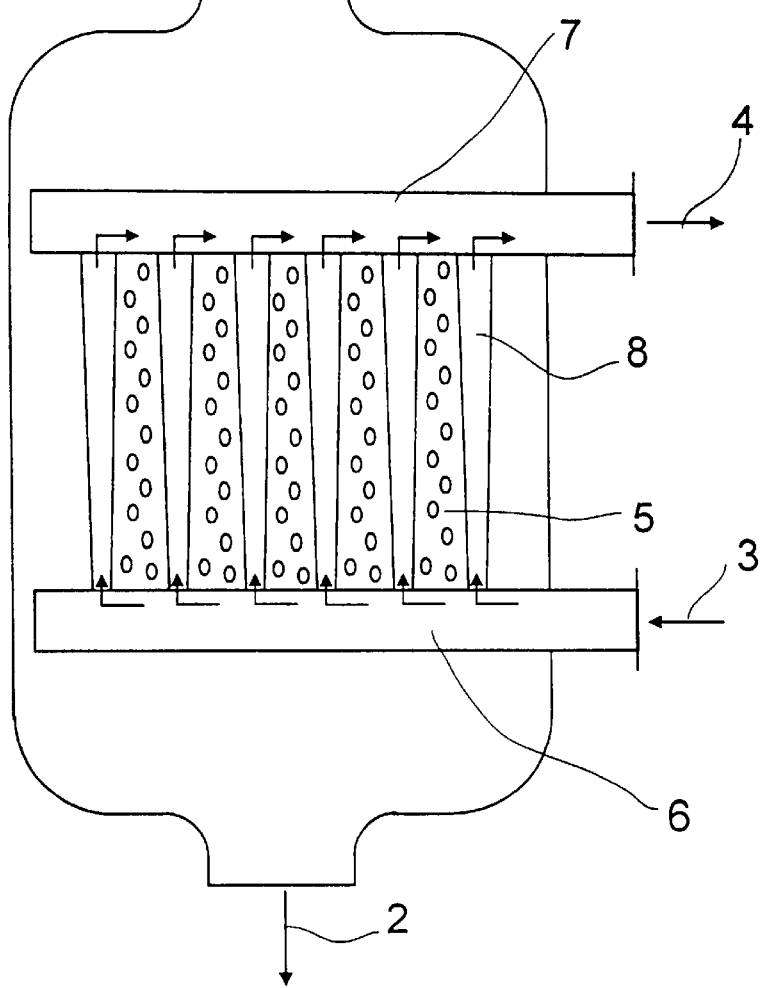
Figure 1B:
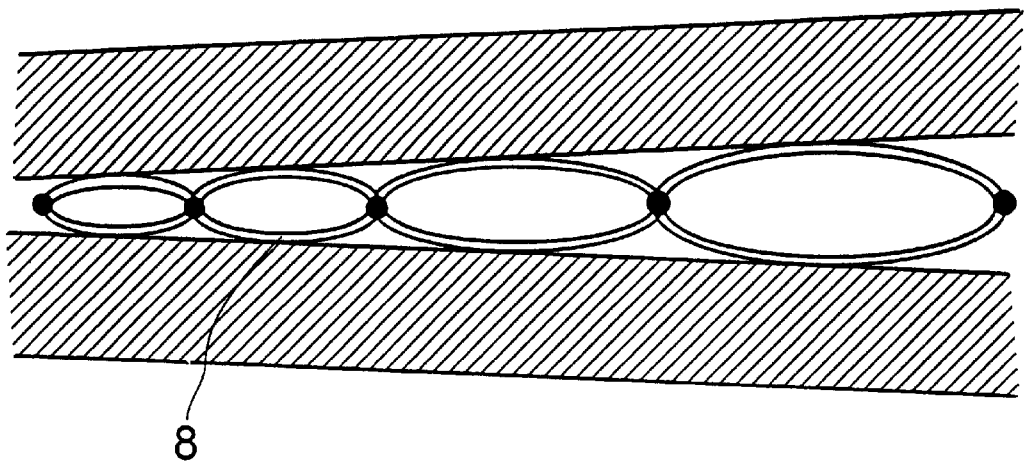
Figure 1C:
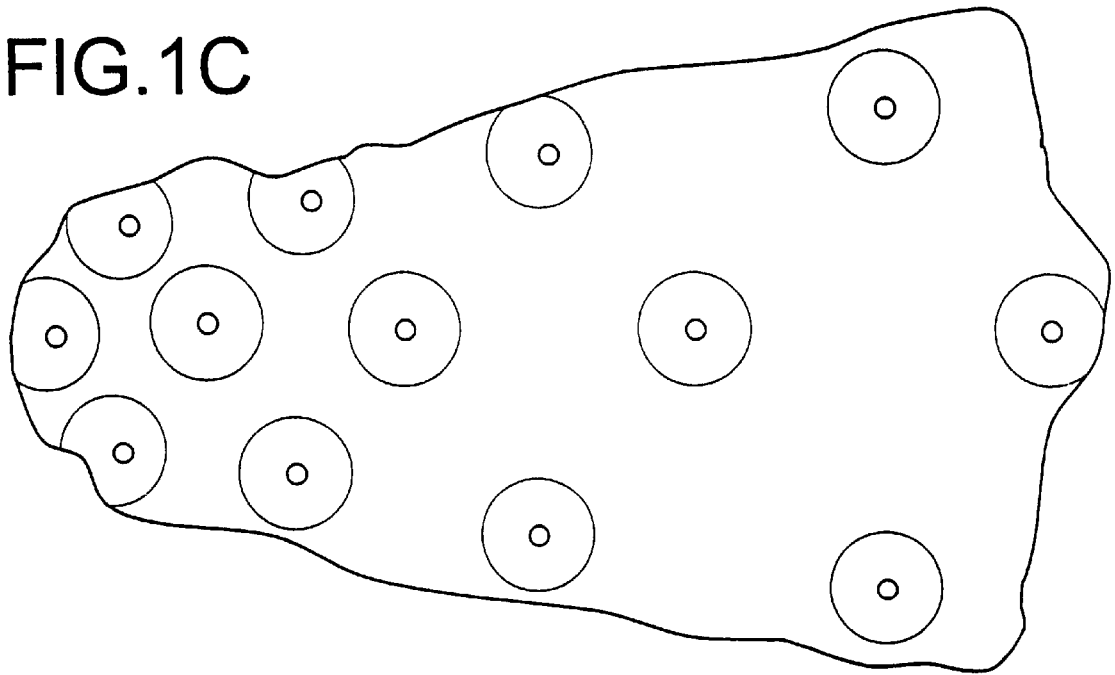
Figure 2:
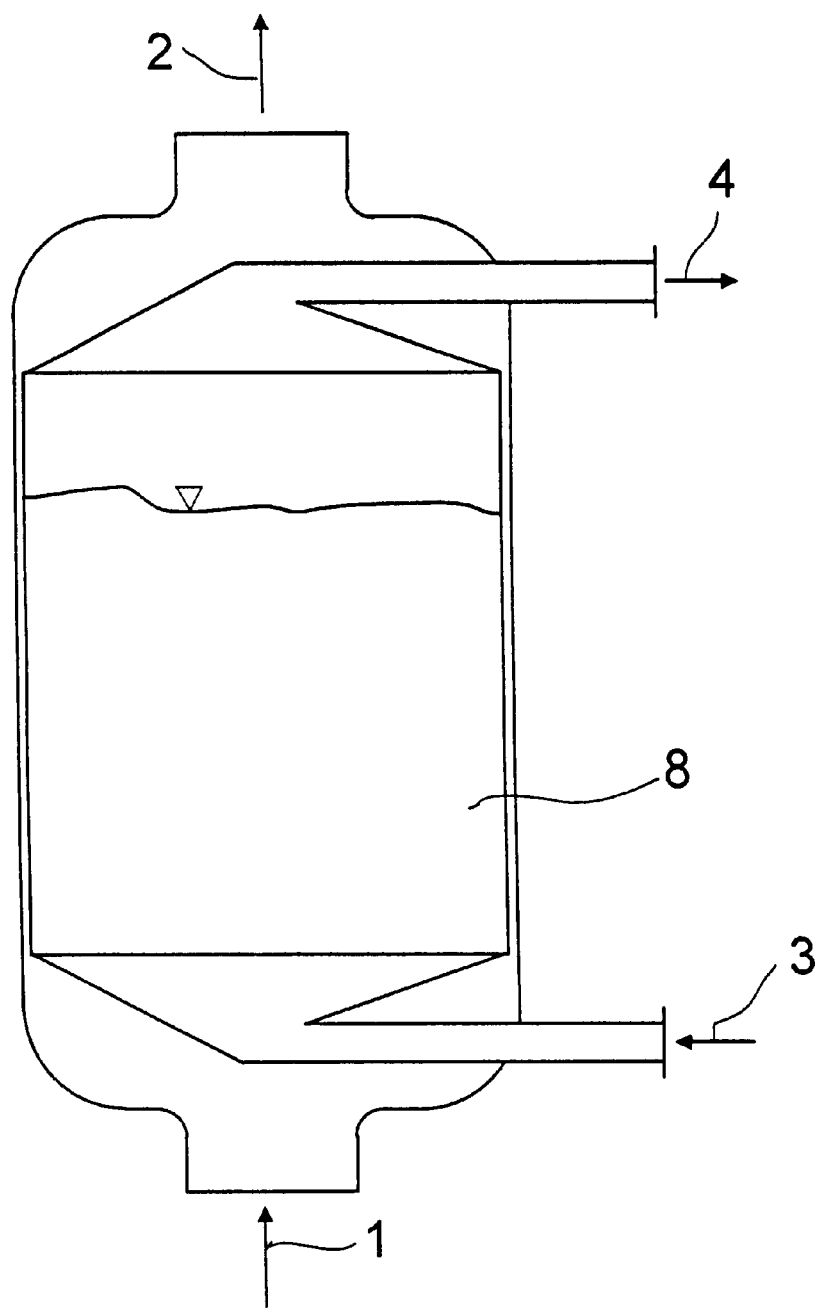
Figure 3:
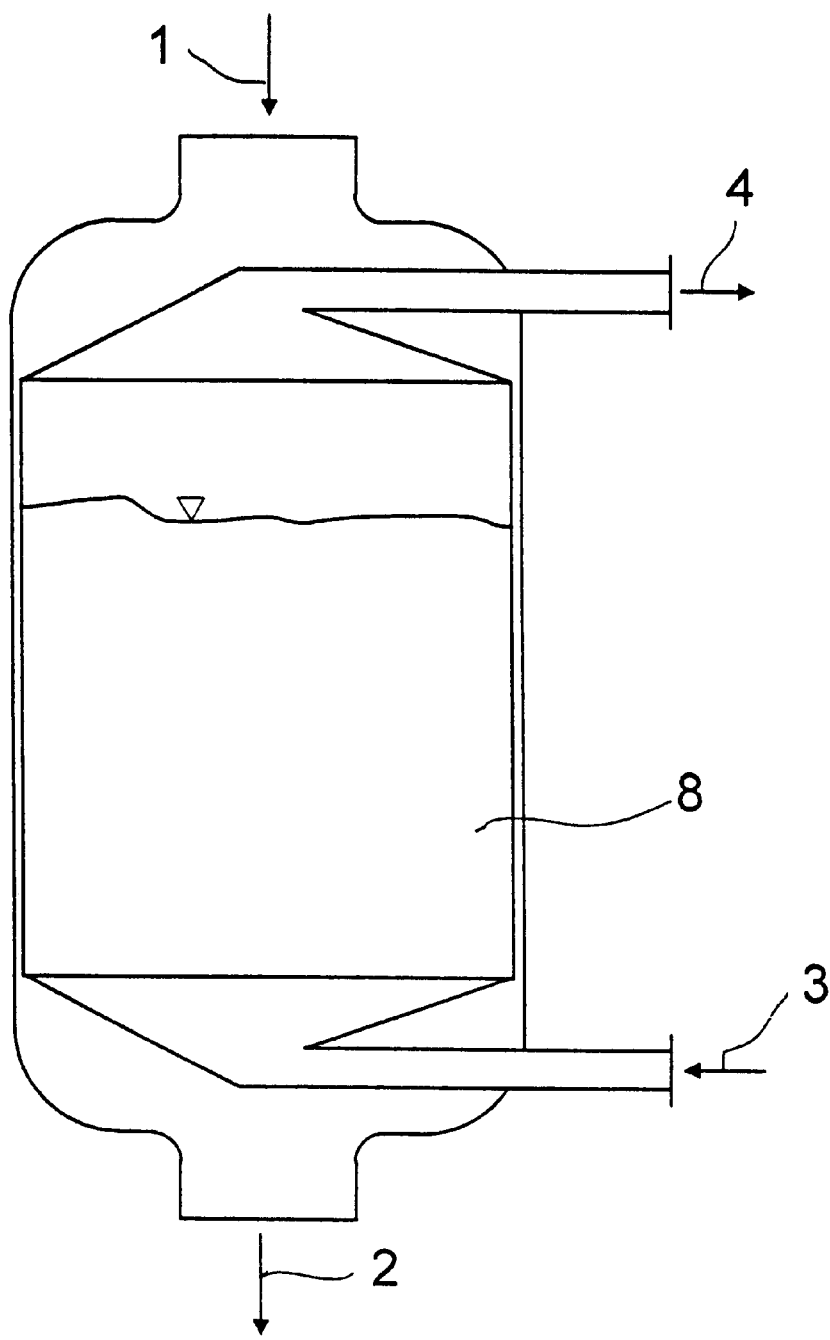
FIG. 3 shows by way of example the reaction mixture and heat-exchange medium flowing in countercurrent.
Figure 4B:
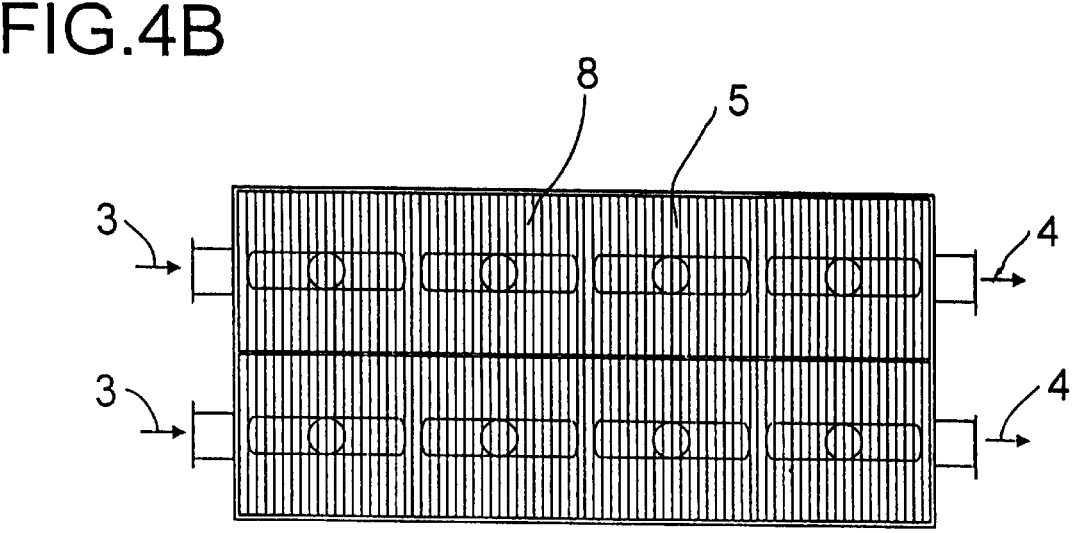
FIG. 4b shows a cross section through the cuboid reactor shown in FIG. 4.
Figure 4:
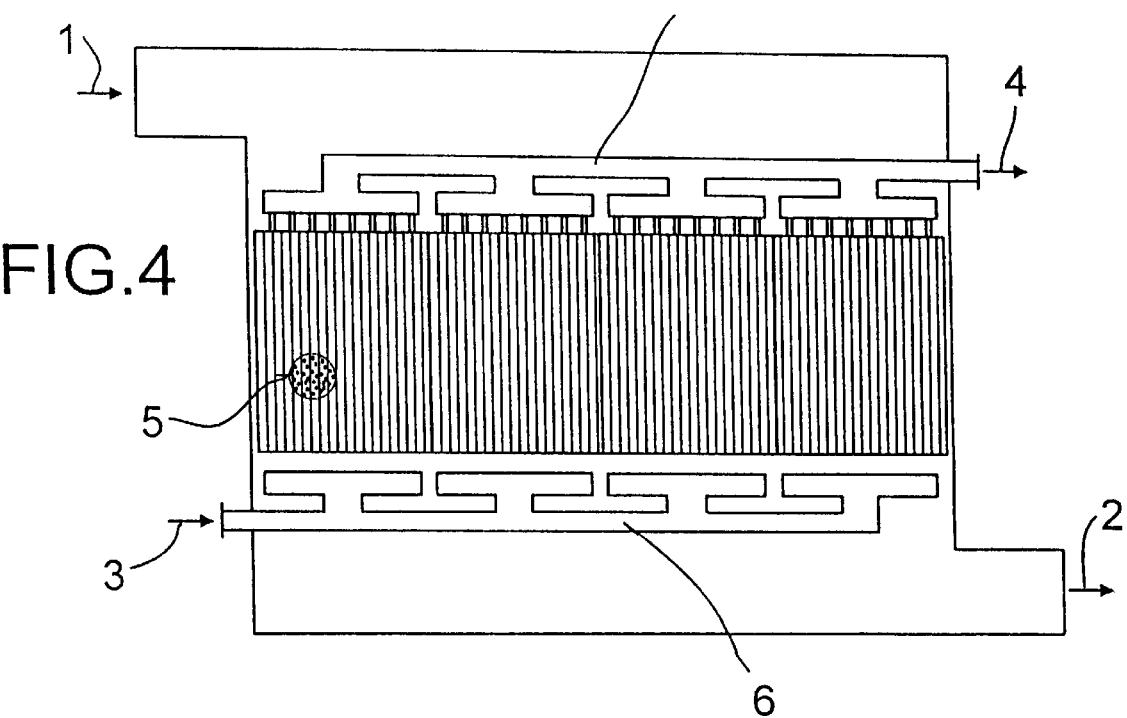
Figure 4A:
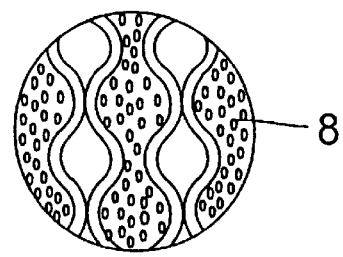
Figure 5:
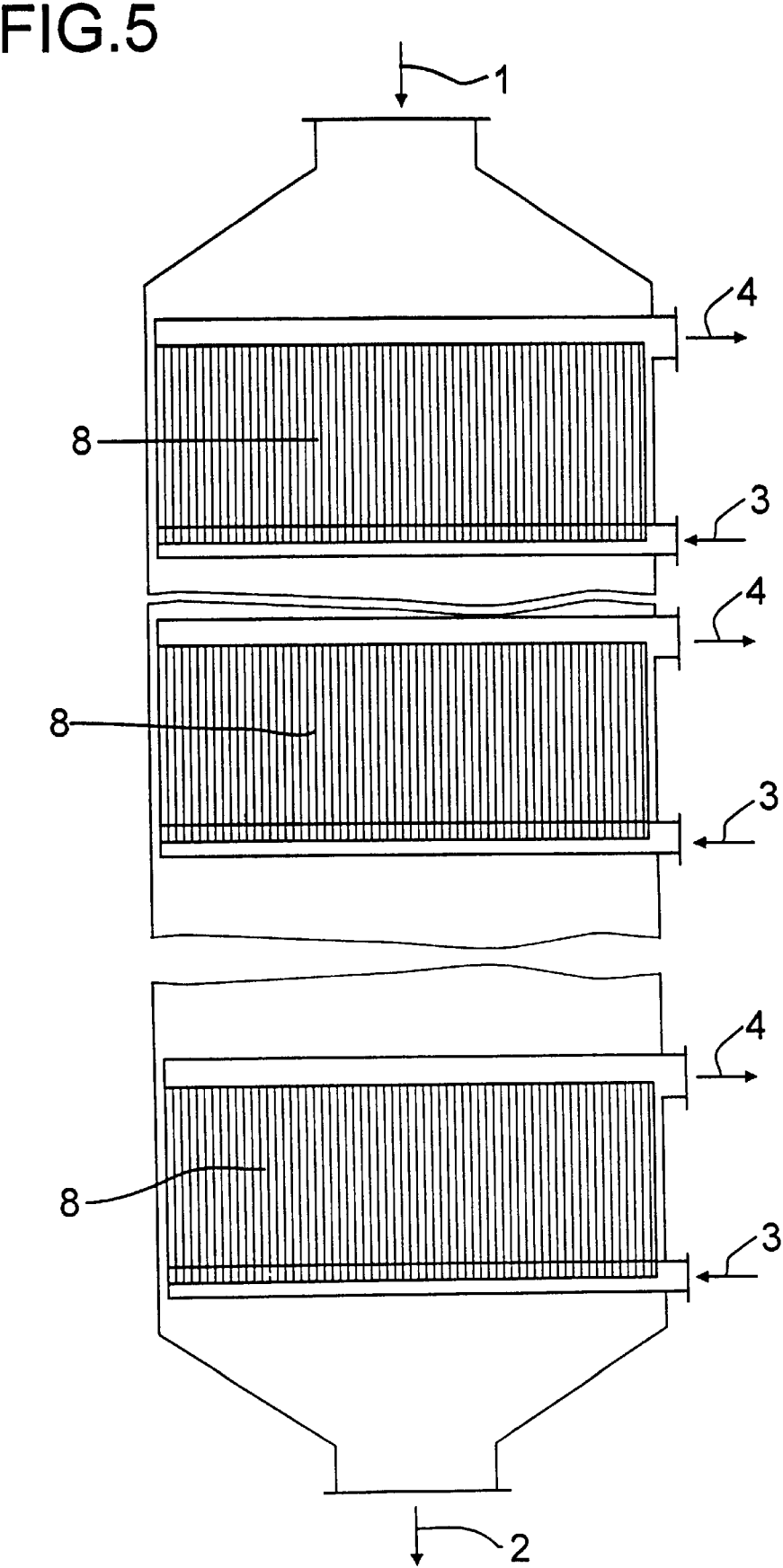

The reactor shown in longitudinal section in FIG. 5 has, by way of example, three reaction zones, each with separate heat-exchange medium circuits.

We claim:

1. A process for the preparation of maleic anhydride by heterogeneously catalyzed gas-phase oxidation in a reactor with feed for the reaction mixture at one end of the reactor and discharge at the opposite end of the reactor, and with devices for dissipating the heat of reaction which are arranged in the reactor interior, wherein the devices are heat-exchanger plates through which a liquid heat-exchange medium flows which evaporates at least partially on flowing through said heat-exchanger plates.

2. A process as claimed in claim 1, wherein the heat-exchanger plates are formed from at least two metal sheets connected in a pressure-tight manner at the periphery and supported against one another in a 15 to 80 mm grid by punctiform bonding and expanded by internal pressure, with the heat-exchange medium flowing through their internal space formed in this way.

3. A process as claimed in claim 2, wherein the heat-exchanger plates are layered to give plane-parallel packages, bent to give rings or ring segments and then arranged concentrically, or bent in a spiral manner.

4. A process as claimed in claim 3, wherein the plate separation of the individual plate packages increases in the flow direction corresponding to the reduction in performance density with increasing reaction progress.

5. A process as claimed in claim 1, wherein a liquid inorganic or organic heat-exchange medium or a gaseous heat-exchange medium is employed.

6. A process as claimed in claim 1, wherein the heat-exchanger plates are arranged parallel to one another.

7. A process as claimed in claim 1, wherein the surfaces of the heat-exchanger plates facing the reaction mixture are provided with a full or partial catalytic coating.

8. A process as claimed in claim 1, wherein reaction mixture comprises n-butane and oxygen.

9. A process as claimed in claim 8, wherein the reaction mixture comprises n-butane, oxygen and further components.

10. A process as claimed in claim 2, wherein the punctiform bonding is spot welding.

* * * * *